United States Patent
Okada et al.

(10) Patent No.: US 8,022,151 B2
(45) Date of Patent: Sep. 20, 2011

(54) ADAMANTANE DERIVATIVE, METHOD FOR PRODUCING THE SAME, RESIN COMPOSITION CONTAINING THE ADAMANTANE DERIVATIVE AND USE THEREOF

(75) Inventors: Yasunari Okada, Chiba (JP); Hidetoshi Ono, Chiba (JP); Katsuki Ito, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 126 days.

(21) Appl. No.: 12/598,041

(22) PCT Filed: Apr. 28, 2008

(86) PCT No.: PCT/JP2008/058178
§ 371 (c)(1),
(2), (4) Date: Oct. 29, 2009

(87) PCT Pub. No.: WO2008/136454
PCT Pub. Date: Nov. 13, 2008

(65) Prior Publication Data
US 2010/0093947 A1  Apr. 15, 2010

(30) Foreign Application Priority Data
May 1, 2007  (JP) .................................. 2007-120998

(51) Int. Cl.
*C08G 59/12* (2006.01)
*C08L 63/00* (2006.01)

(52) U.S. Cl. ......... 525/533; 525/481; 525/523; 528/366

(58) Field of Classification Search ........................ None
See application file for complete search history.

(56) References Cited

U.S. PATENT DOCUMENTS

| 6,066,711 A | 5/2000 | Hanazawa et al. | |
| 2009/0137774 A1 * | 5/2009 | Ito | 528/405 |
| 2009/0137775 A1 | 5/2009 | Ito | |

FOREIGN PATENT DOCUMENTS

| JP | 4 39665 | 2/1992 |
| JP | 6 305044 | 11/1994 |
| JP | 09 302077 | 11/1997 |
| JP | 2003 82062 | 3/2003 |
| JP | 2003 321530 | 11/2003 |
| JP | 2003-321530 A * | 11/2003 |
| JP | 2005 146253 | 6/2005 |
| WO | 2007 010784 | 1/2007 |
| WO | 2007 026828 | 3/2007 |
| WO | 2007/029598 | 3/2007 |
| WO | 2007 094173 | 8/2007 |

OTHER PUBLICATIONS

HCAPLUS accession No. 2007:259728 for WO 2007/026828 and U.S. 2009/0137774, Ito, Mar. 8, 2007, three pages.*
U.S. Appl. No. 12/447,308, filed Jun. 17, 2009, Okada, et al.
Getmanchuk, Yu. et al., "Synthesis and polymerization of adamantil-1-acetic acid glycidyl ester," Ukrainskii Khimicheskii Zhurnal (Russian Edition), vol. 56, No. 5, pp. 551-552, (1990).
Shiryaev, A.K. et al., "Effect of solvent polarity on the conformational equilibrium in glycidyl and thioglycidyl ester", Zhurnal Organicheskoi Khimii, vol. 27, No. 6, pp. 1249-1253, (1991).
Shiryaev, A.K. et al., "Kinetics of the reaction of epichlorohydrin with salts of 1-adamantanecarboxylic acid," Zhurnal Obshchei Khimii, vol. 60, No. 12, pp. 2725-2729, (1990).
Shiryaev, A.K. et al., "Adamantiloxirans and their derivatives:synthesis and antiviral activity", Khimiko-Farmatsevticheskii Zhurnal, vol. 24, No. 5, pp. 23-25, (1990).

* cited by examiner

*Primary Examiner* — Robert Sellers
(74) *Attorney, Agent, or Firm* — Oblon, Spivak, McClelland, Maier & Neustadt, L.L.P.

(57) ABSTRACT

Provided are: an adamantane derivative represented by the following general formula (I) giving a cured product excellent in optical characteristics such as transparency and light resistance, durabilities such as heat resistance, and electrical characteristics such as dielectric constant; a method of producing the adamantane derivative; a resin composition containing the adamantane derivative and an epoxy resin curing agent; and a sealing agent for an optical semiconductor using the resin composition:

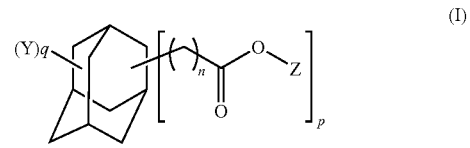

(I)

where: Y represents a group selected from a hydrocarbon group, a hydroxyl group, a carboxyl group, and an =O group formed by two Y's being combined together; Z represents a cyclic ether group; n represents an integer of 0 or more; and p represents an integer of 2 to 4 and q represents an integer of 0 to 14, while satisfying $2 \leq p+q \leq 16$.

6 Claims, No Drawings

ADAMANTANE DERIVATIVE, METHOD FOR PRODUCING THE SAME, RESIN COMPOSITION CONTAINING THE ADAMANTANE DERIVATIVE AND USE THEREOF

TECHNICAL FIELD

The present invention relates to a novel adamantane derivative, a method of producing the same, a resin composition containing the adamantane derivative, and a use thereof. The present invention more specifically relates to: an adamantane derivative giving a cured product that is excellent in optical characteristics such as transparency and light resistance, durabilities such as long-term heat resistance, and electrical characteristics such as dielectric constant, and that is suitable as a sealing agent for an optical semiconductor, an optical electronic member (such as an optical waveguide, a lens for optical communication, or an optical film), a sealing agent and an adhesive agent for an electronic circuit, or the like; a method of producing the adamantane derivative; a resin composition containing the adamantane derivative and an epoxy resin curing agent; and a sealing agent for an optical semiconductor, an optical electronic member, and an sealing agent for an electronic circuit each using the resin composition.

BACKGROUND ART

An optical semiconductor apparatus, which is used widely in a display apparatus, a device for display, or the like, is equipped with a light emitting diode (LED) chip as a light emitting device. In the apparatus, the LED chip is mounted on a light emitting side of a lead frame, is electrically connected with the lead frame by wire bonding, and in addition, is sealed with a resin which protects the light emitting device and also has a function as a lens.

As a sealing material used at the time of sealing the light emitting device such as the LED chip, an epoxy resin is used in many cases for the reasons of its easiness of processability, being transparent, and the like. In the case where a bisphenol A epoxy resin, which is a typical epoxy resin, is used for sealing LED having a short wavelength such as blue, ultraviolet, or white which is a combined color of them, there has been a problem that the bisphenol A epoxy resin absorbs light and turns yellow to be deteriorated, because, in spite of having a heat resistance, the bisphenol A epoxy resin contains an aromatic component. In order to solve the problem, there is proposed an LED sealing agent using a bisphenol A epoxy resin in which an aromatic ring is hydrogenated (refer to Patent Document 1). The hydrogenated bisphenol A epoxy resin is not deteriorated by light, but does not have enough heat resistance to withstand the heat generated at the time of light emission.

On the other hand, an adamantane has a structure in which 4 cyclohexane rings are condensed to form a cage skeleton, and is a highly symmetric and stable compound. Further, a derivative thereof has optical characteristics, heat resistance, and the like, and hence, attempts have been made to use the derivative for an optical disk substrate, an optical fiber, a lens, or the like (refer to Patent Document 2 and Patent Document 3). Further, an attempt has been made to use adamantane esters as a resin raw material for photoresist by utilizing their acid sensitivity, dry etching resistance, ultraviolet transmission property, and the like (refer to Patent Document 4). In addition, a proposal has been made that an epoxy compound derived from adamantane diols is used as a sealing agent for a light emitting diode, and it has been reported that the epoxy resin has heat resistance and light resistance (refer to Patent Document 5). However, the yield of a cyclic ether compound, which is obtained from a reaction of the adamantane diols with a cyclic ether group-containing compound typified by epichlorohydrin, is low resulting from the low reactivity of the adamantane diols. In order to obtain the cyclic ether compound at high yield, it is necessary to go through a complex reaction pathway, and hence, the proposal is not industrially useful.

Patent Document 1: JP 2003-082062 A

Patent Document 2: JP 06-305044 A

Patent Document 3: JP 09-302077 A

Patent Document 4: JP 04-39665 A

Patent Document 5: JP 2005-146253 A

DISCLOSURE OF THE INVENTION

Problems to be solved by the Invention

In view of the above-mentioned circumstances, an object of the present invention is to provide: an adamantane derivative giving a cured product that is excellent in optical characteristics such as transparency and light resistance, durabilities such as long-term heat resistance, and electrical characteristics such as dielectric constant, and that is suitable as a sealing agent for an optical semiconductor, an optical electronic member, a sealing agent and an adhesive agent for an electronic circuit, or the like; a method of producing the adamantane derivative; a resin composition containing the adamantane derivative; and a use thereof.

Means for solving the Problems

The inventors of the present invention have intensively studied and, as a result, have found that the above problems can be solved by using a cyclic ether compound having an adamantane derivative represented by a general formula (I) and a resin composition containing the adamantane derivative and an epoxy resin curing agent, and that the adamantane derivative can be efficiently produced by reacting an adamantane derivative having a corresponding carboxyl group with a compound having a cyclic ether group. Thus, the present invention has been achieved.

That is, the present invention provides the following items (1) to (5):

(1) an adamantane derivative represented by the following general formula (I):

[Chem 1]

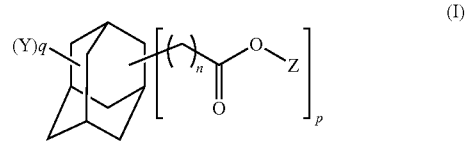

where: Y represents a group selected from a hydrocarbon group having 1 to 10 carbon atoms, a hydroxyl group, a carboxyl group, and an =O group formed by two Y's being combined together, and a plurality of Y's may be identical to or different from each other;

Z is represented by the following general formula (II) or (III):

[Chem 2]

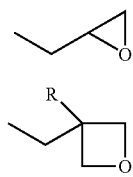

where R represents a hydrogen atom or an alkyl group having 1 to 4 carbon atoms;
n represents an integer of 0 or more; and p represents an integer of 2 to 4 and q represents an integer of 0 to 14, while satisfying $2 \leq p+q \leq 16$, provided that n=0 and p=2 are not satisfied at the same time;

(2) a method of producing the adamantane derivative according to the item (1), including reacting an adamantane derivative having a carboxyl group represented by the following general formula (IV) with a compound having a cyclic ether group represented by the following general formula (V) or (VI):

[Chem 3]

where Y, n, p, q, and p+q each represent the same as above; and

[Chem 4]

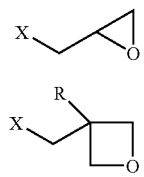

where X represents a halogen atom, a mesyl group, or a tosyl group, and R represents the same as above;

(3) a resin composition, including: the adamantane derivative according to the item (1); and an epoxy resin curing agent;

(4) a sealing agent for an optical semiconductor, which is formed by using the resin composition according to the item (3); and (5) an optical electronic member, which is formed by using the resin composition according to the item (3).

Effects Of the Invention

The adamantane derivative of the present invention is a cyclic ether compound having an adamantane skeleton, and hence is excellent in heat resistance and adhesive property and also has etching resistance.

Further, the resin composition of the present invention containing the adamantane derivative and an epoxy resin curing agent gives a cured product that is excellent in optical characteristics such as transparency and light resistance, and in addition, durabilities such as heat resistance and electrical characteristics such as dielectric constant. Therefore, the resin composition can be suitably used as a sealing agent for an optical semiconductor, an optical electronic member (such as an optical waveguide, a lens for optical communication, or an optical film), a sealing agent and an adhesive agent for an electronic circuit, or the like.

Best Mode for Carrying Out the Invention

An adamantane derivative of the present invention is a compound represented by a general formula (I), and hereinafter, the compound and a method of producing the compound are described.

[Adamantane Derivative]

First, the adamantane derivative of the present invention is a compound having a structure represented by the following general formula (I):

[Chem 5]

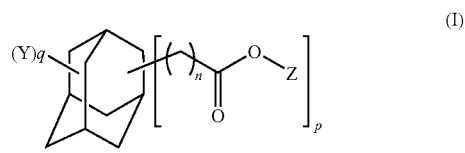

where: Y represents a group selected from a hydrocarbon group having 1 to 10 carbon atoms, a hydroxyl group, a carboxyl group, and an =O group formed by two Y's being combined together, and a plurality of Y's may be identical to or different from each other; n represents an integer of 0 or more; and p represents an integer of 2 to 4 and q represents an integer of 0 to 14, while satisfying $2 \leq p+q \leq 16$, provided that n=0 and p=2 are not satisfied at the same time.

The hydrocarbon group having 1 to 10 carbon atoms represented by Y may be a linear or branched alkyl group, and examples thereof include a methyl group, an ethyl group, various propyl groups, various butyl groups, various pentyl groups, various hexyl groups, various heptyl groups, various octyl groups, various nonyl groups, and various decyl groups. Further, the hydrocarbon group may be an alkoxy group such as a methoxy group or an ethoxy group.

In the above general formula (I), Z represents a group represented by the following general formula (II) or (III).

[Chem 6]

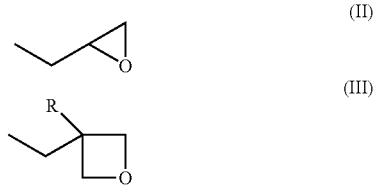

In the above general formula (III), R represents a hydrogen atom or an alkyl group having 1 to 4 carbon atoms. The alkyl group having 1 to 4 carbon atoms may be linear or branched, and examples thereof include a methyl group, an ethyl group, various propyl groups, and various butyl groups.

Examples of preferable compounds represented by the above general formula (I) include 1,3,5-adamantanetricarboxylic acid triglycidyl ester, 1,3,5,7-adamantanetetracarboxylic acid tetraglycidyl ester, 1,3-adamantanediacetic acid diglycidyl ester, 1,3,5-adamantanetriacetic acid triglycidyl ester, and 1,3,5,7-adamantanetetraacetic acid tetraglycidyl ester.

[Method of Producing Adamantane Derivative]

Next, a method of producing the adamantane derivative of the present invention is described.

The adamantane derivative represented by the above general formula (I) can be synthesized by reacting (esterifying) an adamantane derivative having a carboxyl group represented by the following general formula (IV):

[Chem 7]

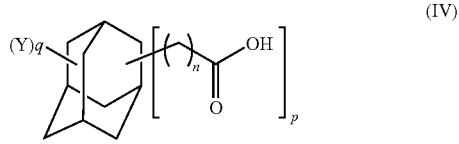

(IV)

where Y, n, p, q, and p+q each represent the same as above, with a compound having a cyclic ether group represented by the following general formula (V) or (VI):

[Chem 8]

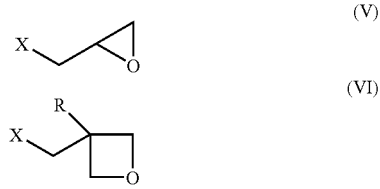

(V)

(VI)

where X represents a halogen atom, a mesyl group, or a tosyl group, and R represents the same as above.

Examples of the adamantane derivative having a carboxyl group represented by the above general formula (IV) include 1,3-adamantanediacetic acid, 1,3-adamantanedipropionic acid, 1,3,5-adamantanetricarboxylic acid, 1,3,5-adamantanetriacetic acid, 1,3,5-adamantanetripropionic acid, 1,3,5,7-adamantanetetracarboxylic acid, 1,3,5,7-adamantanetetraacetic acid, and 1,3,5,7-adamantanetetrapropionic acid.

Examples of the compound having a cyclic ether group represented by the above general formula (V) or (VI) include epichlorohydrin, epibromohydrin, 3-chloromethyl-3-methyloxetane, 3-chloromethyl-3-ethyloxetane, 3-methylsulfonyl oxymethyl-3-methyloxetane, and 3-p-tolulenesulfonyl oxy methyl-3-methyloxetane.

The reaction of the adamantane derivative having a carboxyl group with the compound having a cyclic ether group can be performed under the presence of a base catalyst.

Examples of the base catalyst include sodium amide, triethylamine, tributylamine, trioctylamine, pyridine, N,N-dimethylaniline, 1,5-diazabicyclo[4.3.0]nonene-5 (DBN), 1,8-diazabicyclo[5.4.0]undecene-7 (DBU), tetramethylammonium chloride (bromide), tetraethylammonium chloride (bromide), sodium hydroxide, potassium hydroxide, sodium hydride, sodium phosphate, potassium phosphate, sodium carbonate, potassium carbonate, silver oxide, sodium methoxide, and potassium t-butoxide. Further, those base catalysts may be used alone or in combination.

The amount of the base catalyst is generally 0.5 to 10 mol % and preferably 1 to 5 mol % with respect to the adamantane derivative having a carboxyl group.

The reaction may be carried out in the absence or presence of a solvent. As the solvent, a solvent having preferably 0.5 mass % or more and more preferably 5 mass % or more of solubility of the adamantane derivative having a carboxyl group is used. The amount of the solvent to be used is such that the concentration of the adamantane derivative having a carboxyl group is preferably 0.5 mass % or more and more preferably 5 mass % or more. Here, the adamantane derivative may exist in the state of suspension but is desirably in the state of solution. Specific examples include hexane, heptane, toluene, dimethylformamide (DMF), dimethylacetamide (DMAc), dimethylsulfoxide (DMSO), ethyl acetate, diethyl ether, tetrahydrofuran, acetone, methyl ethyl ketone, and methyl isobutyl ketone. Further, those solvents may be used alone or in combination.

The reaction temperature is generally 0 to 200° C. In the case where the temperature is too low, a reaction rate lowers, and when the temperature is too high, coloring becomes significant. The reaction temperature is preferably 20 to 150° C.

The reaction pressure is generally 0.01 to 10 MPa in terms of absolute pressure. In the case where the pressure is too high, security problems arise, which requires a special apparatus, and hence, it is not preferred. The reaction pressure is preferably normal pressure to 1 MPa.

The reaction time cannot be categorically decided, because the reaction time depends on the kind and amount of the base catalyst, the reaction temperature, and the like, but is generally 1 minute to 24 hours and more preferably 1 to 10 hours.

In the reaction of the present invention, it is preferred that the following method be adopted: the water generated in the reaction is removed from the reaction system, to thereby transfer an equilibrium reaction to a generation system.

In general, the compound having a cyclic ether group contains a dimeric or higher oligomer component, and also in the above reaction, a dimeric or higher oligomer of an adamantane derivative having a cyclic ether group is generated. The presence of the oligomer in the reaction is not problematic, but when the oligomer of an adamantane derivative is removed as the need arises, the reaction product can be purified. As a purification method, there can be employed distillation, crystallization, column separation, and the like, and the purification method can be selected depending on the property of the product and the kind of impurities.

In the esterification reaction of the adamantane derivative having a carboxyl group with the compound having a cyclic ether group, in the case where the generation of the adamantane derivative having a cyclic ether group represented by the general formula (I), which is a reaction product, is insufficient, the reaction product is subjected to a reaction again under the following reaction conditions in the presence of a base catalyst, to thereby perform a ring closure reaction, and as a result, the content of the cyclic ether group can be increased, and in addition, the yield of the adamantane derivative represented by the general formula (I) can be increased.

Examples of the base catalyst include sodium hydroxide, potassium hydroxide, sodium phosphate, potassium phosphate, sodium carbonate, potassium carbonate, calcium hydroxide, and magnesium hydroxide. The amount of the base catalyst is generally 0.1 to 20 mol % and preferably 1 to 10 mol % with respect to the reaction product containing a compound in which the ring of the cyclic ether group is opened. In the case where the amount of the base catalyst is small, the reaction time is lengthened, and in the case where the amount of the base catalyst is large, there is no particular problem but the effect corresponding to the amount cannot be obtained.

As the solvent to be used in the ring closure reaction, a solvent having preferably 0.5 mass % or more and more preferably 5 mass % or more of solubility of the reaction product therein is used. The amount of the solvent to be used is such that the concentration of the reaction product therein is preferably 0.5 mass % or more and more preferably 5 mass % or more. Here, the reaction product may exist in the state of suspension but is desirably in the state of solution. Specific examples include hexane, heptane, toluene, DMF, DMAc, DMSO, ethyl acetate, diethyl ether, tetrahydrofuran, acetone, methyl ethyl ketone, and methyl isobutyl ketone. Further, those solvents may be used alone or in combination.

The reaction temperature of the ring closure reaction is generally 20 to 200° C. In the case where the temperature is too low, a reaction rate lowers, and when the temperature is too high, coloring becomes significant. The reaction temperature is preferably 30 to 150° C.

The reaction pressure of the ring closure reaction is generally 0.01 to 10 MPa in terms of absolute pressure. In the case where the pressure is too high, security problems arise, which requires a special apparatus, and hence, it is not preferred. The reaction pressure is preferably normal pressure to 1 MPa.

The reaction time of the ring closure reaction cannot be categorically decided, because the reaction time depends on the kind and amount of the base catalyst, the reaction temperature, and the like, but is generally 1 minute to 24 hours and more preferably 30 minutes to 10 hours.

As the purification method of the reaction product, there can be employed, as described above, distillation, crystallization, column separation, and the like, and the purification method can be selected depending on the property of the product and the kind of impurities.

[Resin Composition Containing Adamantane Derivative and Epoxy Resin Curing Agent]

For a resin composition of the present invention, the adamantane derivative having a cyclic ether group represented by the above general formula (I) may be used alone, and from the viewpoint of optimizing the mechanical strength, the solubility, the workability, and the like, it is preferred to use the mixture of the adamantane derivative and another epoxy resin for the resin composition.

Hereinafter, an adamantane derivative and an adamantane derivative containing, as needed, another epoxy resin and an epoxy resin curing agent may be simply referred to as resin composition.

Examples of the another epoxy resin include: a bisphenol A epoxy resin, a bisphenol F epoxy resin, a bisphenol S epoxy resin (bisphenol A diglycidyl ether, bisphenol AD diglycidyl ether, bisphenol S diglycidyl ether, bisphenol F diglycidyl ether, bisphenol G diglycidyl ether, tetramethylbisphenol A diglycidyl ether, bisphenol hexafluoroacetone diglycidyl ether, bisphenol C diglycidyl ether, and the like); novolak epoxy resins such as a phenol novolak epoxy resin and a cresol novolak epoxy resin; alicyclic epoxy resins such as 3,4-epoxycyclohexylmethyl-3,4-epoxycyclohexylcarboxylate; nitrogen-containing heterocyclic epoxy resins such as triglycidyl isocyanurate and a hydantoin epoxy resin; a hydrogenated bisphenol A epoxy resin; an aliphatic epoxy resin; a biphenyl epoxy resin, a dicyclo-type cyclic epoxy resin, and a naphthalene epoxy resin, which are a mainstream of a low water-absorption curing type; polyfunctional epoxy resins such as trimethylolpropane polyglycidyl ether, glycerol polyglycidyl ether, and pentaerythritol polyglycidyl ether; fluorine-containing epoxy resins such as a bisphenol AF epoxy resin; and a (meth)acrylate diglycidyl ester. Further, those epoxy resins may be used alone or in a combination of two or more kinds.

The above epoxy resin may be solid or liquid at normal temperature, but in general, the epoxy resin preferably has an average epoxy equivalent of 100 to 2,000. In the case where the average epoxy equivalent is less than 100, a cured product of the resin composition of the present invention may become fragile. Further, in the case where the average epoxy equivalent exceeds 2,000, the glass transition temperature (Tg) of the cured product may become low.

[Epoxy Resin Curing Agent]

Examples of the epoxy resin curing agent of the present invention include a cationic polymerization initiator, an acid anhydride curing agent, a phenolic curing agent, and an amine curing agent.

As the cationic polymerization initiator, a cationic polymerization initiator which may react with the epoxy group of the adamantane derivative having an epoxy group by heat or UV light may be used. Examples of the initiator include: aromatic diazonium salts such as p-methoxybenzenediazonium hexafluorophosphate; aromatic sulfonium salts such as triphenylsulfonium hexafluorophosphate; aromatic iodonium salts such as diphenyliodonium hexafluorophosphate; an aromatic iodosyl salt; an aromatic sulfoxonium salt; and a metallocene compound. Of those, aromatic sulfonium salts such as triphenylsulfonium hexafluorophosphate and aromatic iodonium salts such as diphenyliodonium hexafluorophosphate may be most suitable.

The blending amount of the cationic polymerization initiator is preferably 0.01 to 5.0 mass % and more preferably 0.1 to 3.0 mass % with respect to the resin composition of the present invention. When the blending amount is set within the above range, satisfactory polymerization and physical properties such as optical characteristics can be realized.

Examples of the acid anhydride curing agent include phthalic anhydride, maleic anhydride, trimellitic anhydride, pyromellitic anhydride, haxahydrophthalic anhydride, tetrahydrophthalic anhydride, methylnadic anhydride, nadic anhydride, glutaric anhydride, methylhexahydrophthalic anhydride, and methyltetrahydrophthalic anhydride. Of those, haxahydrophthalic anhydride, tetrahydrophthalic anhydride, methylhexahydrophthalic anhydride, and methyltetrahydrophthalic anhydride are most suitable. Further, in the case where an acid anhydride is used, a curing accelerator may be blended thereinto for the purpose of accelerating the curing of the acid anhydride. Examples of the curing accelerator include the compounds exemplified in the description of additives described below.

Examples of the phenolic curing agent include a phenol novolak resin, a cresol novolak resin, a bisphenol A novolak resin, and a triazine-modified phenol novolak resin.

Examples of the amine curing agent include dicyandiamide and aromatic diamines such as m-phenylenediamine, 4,4'-diaminodiphenylmethane, 4,4'-diaminodiphenylsulfone, and m-xylylenediamine.

Those curing agents may be used alone or in a combination of two or more kinds.

Further, the resin composition of the present invention into which those curing agents are blended comes to have, by being cured, excellent heat resistance and transparency, and in addition, is improved in light resistance, dielectric constant, and the like.

Of those curing agents, an acid anhydride curing agent is preferred for a sealing agent for an optical semiconductor from the viewpoint of physical properties such as transparency of a cured resin. Of the acid anhydride curing agents, haxahydrophthalic anhydride, tetrahydrophthalic anhydride, methylhexahydrophthalic anhydride, and methyltetrahydrophthalic anhydride are most preferred.

[Additive]

Further, into the resin composition of the present invention, there may be appropriately blended, as needed, various additives that have been used conventionally, such as a curing accelerator, a decay-preventing agent, a modifying agent, a silane coupling agent, a defoaming agent, an inorganic powder, a solvent, a leveling agent, a release agent, a dye, and a pigment.

Examples of the curing accelerator include but are not particularly limited to: tertiary amines such as 1,8-diazabicyclo[5.4.0]undecene-7-triethylenediamine and tris(2,4,6-dimethylaminomethyl)phenol; imidazoles such as 2-ethyl-4-methylimidazole and 2-methylimidazole; phosphorous compounds such as triphenylphosphine, tetraphenylphosphonium bromide, tetraphenylphosphonium tetraphenylborate, and tetra-n-butylphosphonium-O,O-diethylphosphorodithioate; a quaternary ammonium salt; organic metal salts; and derivatives thereof. Those may be used alone or two or more kinds thereof may be used in combination. Of those curing accelerators, it is preferred to use tertiary amines, imidazoles, and phosphorous compounds.

The blending amount of the curing accelerator is preferably 0.01 to 8.0 mass % and more preferably 0.1 to 3.0 mass % with respect to the resin composition of the present invention. When the blending amount of the curing accelerator is set within the above range, sufficient curing accelerating effect can be obtained, and discoloration is not observed in the obtained cured product.

The resin composition of the present invention is excellent in heat resistance and transparency, and in order to maintain those properties, a decay-preventing agent may be added. Examples of the decay-preventing agent include decay-preventing agents such as a phenolic compound, an amine compound, an organic sulfur compound, and a phosphorous compound.

Examples of the phenolic compound include commercially available products such as Irganox 1010 (trademark, manufactured by Ciba Specialty Chemicals Inc.), Irganox 1076 (trademark, manufactured by Ciba Specialty Chemicals Inc.), Irganox 1330 (trademark, manufactured by Ciba Specialty Chemicals Inc.), Irganox 3114 (trademark, manufactured by Ciba Specialty Chemicals Inc.), Irganox 3125 (trademark, manufactured by Ciba Specialty Chemicals Inc.), Irganox 3790 (trademark, manufactured by Ciba Specialty Chemicals Inc.), BHT, Cyanox 1790 (trademark, manufactured by Cyanamid Co.), and Sumilizer GA-80 (trademark, manufactured by Sumitomo Chemical Co., Ltd.).

Examples of the amine compound include: Irgastab FS042 (trademark, manufactured by Ciba Specialty Chemicals Inc.); GENOX EP (trademark, manufactured by Crompton Corp., compound name: dialkyl-N-methylamine oxide); and hindered amine compounds such as ADK STAB LA-52, LA-57, LA-62, LA-63, LA-67, LA-68, LA-77, LA-82, LA-87, and LA-94, all manufactured by Asahi Denka Co., Ltd., Tinuvin 123, 144, 440, 662, Chimassorb 2020, 119, and 944, all manufactured by Ciba Specialty Chemicals Inc., Hostavin N30 manufactured by Hoechst GmbH, Cyasorb UV-3346 and UV-3526, both manufactured by Cytec Industries Inc., Uval 299 manufactured by Great Lakes Chemical Corp., and Sanduvor PR-31 manufactured by Clariant Corp.

Examples of the organic sulfur compound include commercially available products such as DSTP (Yoshitomi) (trademark, manufactured by Yoshitomi Pharmaceutical Co., Ltd.), DLTP (Yoshitomi) (trademark, manufactured by Yoshitomi Pharmaceutical Co., Ltd.), DLTOIB (trademark, manufactured by Yoshitomi Pharmaceutical Co., Ltd.), DMTP (Yoshitomi) (trademark, manufactured by Yoshitomi Pharmaceutical Co., Ltd.), Seenox 412S (trademark, manufactured by Shipro Kasei, Ltd.), and Cyanox 1212 (trademark, manufactured by Cyanamid Co.).

Examples of the modifying agent include modifying agents such as glycols, silicones, and alcohols. Examples of the silane coupling agent include silane coupling agents such as a silane type and a titanate type. Examples of the defoaming agent include defoaming agents such as a silicone type. Examples of the inorganic powder include inorganic powders such as glass powder, silica powder, titania, zinc oxide, and alumina each having a particle diameter of several nanometers to 10 µm depending on their use. Examples of the solvent that may be used for epoxy resin powder and as a diluent solvent for coating include: aromatic solvents such as toluene and xylene; and ketone solvents such as methyl ethyl ketone, methyl isobutyl ketone, and cyclohexanone.

[Cured Product of Resin Composition Containing Adamantane Derivative and Epoxy Resin Curing Agent]

The resin composition of the present invention is obtained by blending the adamantane derivative with, as needed, an epoxy resin, and an epoxy resin curing agent, or a cationic polymerization initiator, various additives, and the like. Then, the resin composition is formed into a desired shape by being injected into a die (resin die) or by being subjected to coating, and after that, the resultant is subjected to heat curing or ultraviolet curing.

The curing temperature is generally 50 to 200° C. and preferably 100 to 180° C. When the curing temperature is set to 50° C. or higher, curing failure does not occur, and when the curing temperature is set to 200° C. or lower, coloring or the like does not occur. The curing time differs depends on the kinds of the epoxy resin, the curing agent, the accelerator, and the initiator to be used, and is preferably 0.5 to 6 hours.

The irradiation intensity of ultraviolet ray is generally about 500 to 5,000 mJ/cm$^2$ and preferably 1,000 to 4,000 mJ/cm$^2$. After the ultraviolet irradiation, the resultant may be heated, and it is preferred that the heating be performed at about 70 to 200° C. for about 0.5 to 12 hours. A molding method for the resultant is not particularly limited, and examples thereof include injection molding, blow molding, and press molding.

The cured product obtained by curing the resin composition of the present invention is excellent in optical characteristics such as transparency and light resistance, and has a total light transmittance of generally 70% or more. Further, as shown in examples below, the cured product is excellent in processability because of its low dissolution temperature, and there can be obtained a cured product which has high glass transition temperature and is excellent in durabilities such as heat resistance and light resistance, and in addition, electrical characteristics such as dielectric constant.

As described above, the resin composition of the present invention has excellent characteristics, and hence is used for a semiconductor element/an integrated circuit (IC or the like), an individual semiconductor (diode, transistor, thermistor, or the like), an LED (LED lamp, chip LED, light receiving element, lens for an optical semiconductor, or the like), a sensor (temperature sensor, light sensor, or magnetic sensor), a passive component (high frequency device, resistor, condenser, or the like), a structural component (connector, switch, relay, or the like), an automobile part (circuit system, control system, sensors, lamp seal, or the like), an adhesive agent (optical component, optical disk, or pickup lens), and the like, and, in addition, for an optical film and the like as surface coating.

Therefore, the resin composition of the present invention is suitably used for the optical electronic members such as a lens for optical communication and an optical film, as the sealing agent and the adhesive agent for an optical semiconductor (such as LED), an organic EL device, an optical circuit (optical waveguide), and an electronic circuit.

Further, the resin composition of the present invention has an adamantane skeleton, and hence is excellent in heat resistance and adhesive property, and also has etching resistance. Therefore, the resin composition is also useful as semiconductor forming materials such as a sealing agent for a semiconductor and an anti-reflection film for a semiconductor.

A construction as the sealing agent for an optical semiconductor may be applied to a device of a bombshell type, a surface mount type (SMT), or the like, may adhere well with semiconductors such as GaN formed on a metal or a polyamide, and further may be used by dispersing fluorescent dyes such as YAG therein. Further, it may be used also for a surface coating material of a bomb shell type LED and for a lens of an SMT type LED, and the like.

A construction for an organic EL is applicable to the organic EL device having a construction of anode/hole-injection layer/luminescent layer/electron-injection layer/cathode which is formed in the stated order on general transparent substrates such as glasses and transparent resins. The sealing agent may be used as an adhesive agent in covering an organic EL device with a metal can, a metal sheet, or a resin film coated with SiN and the like as a sealing agent of an organic EL device, or an organic EL device may be directly sealed by dispersing inorganic fillers and the like in the epoxy resin of the present invention in order to impart gas-barrier properties. The sealing agent may be applied to a bottom emission type, which is currently a mainstream as a display system, but the effects of transparency and heat resistance of the resin composition of the present invention may be advantageously utilized when applied to a top emission type, which will draw attention in the future in view of the light extraction efficiency.

A construction for an optical circuit is applicable to a thermooptic switch and an arrayed waveguide grating for a single-mode and a multi-mode, to an optical multiplexer/demultiplexer, to a wavelength-variable filter, or to a core material and a clad material for an optical fiber. Further, it is also applicable to a micro lens array focusing a light to a waveguide and to a mirror of an MEMS-type optical switch. Further, it is also applicable to a dye binder and the like for a photoelectric transducer.

A construction for an electronic circuit is applicable as an interlayer insulation film, as an adhesive agent between a polyimide and a copper foil for a flexible printed board, or as a resin for a substrate.

A construction for an optical film is applicable as a display of film substrates for liquid crystal and for organic EL device, or as a light diffusion film, an anti-reflection film, a color-converting film using dispersion of a fluorescent dye and the like.

EXAMPLES

Hereinafter, the present invention is more specifically described by way of examples and comparative examples, but the present invention is not limited by those examples.

Synthesis of Adamantane Derivative

Example 1

Synthesis of 1,3,5-adamantanetricarboxylicacidtriglycidyl ester

30 G (0.11 mol) of 1,3,5-adamantanetricarboxylic acid triglycidyl, 124 g (1.30 mmol) of epichlorohydrin, 3 g of tetraethylammonium bromide, 90 g of toluene, and 40 g of a 50 mass % sodium hydroxide aqueous solution were charged into a 300-mL round bottom flask equipped with a Dean-Stark reflux condenser, a stirrer, a thermometer, and a nitrogen introducing tube. The flask was immersed in an oil bath at 130° C. and was heated to reflux for 5 hours. At that time, a small amount of nitrogen was allowed to flow and the mixture was stirred, and the reaction was performed while removing from the reaction system the water generated along with the progress of the reaction. After that, the reaction solution was cooled to room temperature and washed with water until the aqueous layer became neutral, and then the solvent was distilled off from the organic layer, to thereby obtain an yellow viscous liquid.

Next, the yellow viscous liquid was dissolved in 175 g of toluene, and 10.5 g of a 25 mass % sodium hydroxide aqueous solution were added thereto. The mixture was stirred and heated to reflux in an oil bath at 130° C. for 2 hours. After that, the resultant was cooled to room temperature and washed with water until the alkali aqueous layer became neutral, and then the aqueous layer was further washed with water once more. The solvent was distilled off from the organic layer, to thereby obtain a target product represented by the following formula (yield: 84%, epoxy equivalent of 168).

[Chem 9]

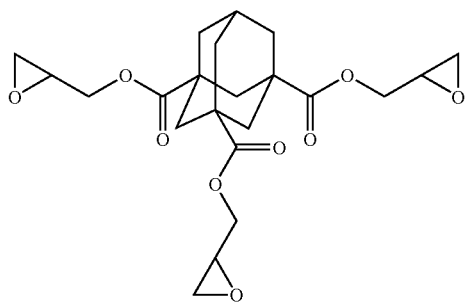

Nuclear magnetic resonance spectra (solvent: $CDCl_3$) JNM-ECA500 manufactured by JEOL LTD.

$^1$H-NMR (500 MHz): 1.88 (s, 6H), 2.07 (m, 6H), 2.33 (s, 1H), 2.64 (dd, 3H), 2.84 (dd, 3H), 3.20 (m, 3H), 3.94 (dd, 3H), 4.42 (dd, 3H)

$^{13}$C-NMR (125 MHz): 27.8, 37.0, 39.0, 41.4, 44.5, 49.3, 65.1, 175.4

Example 2

Synthesis of 1,3-adamantanediacetic acid diglycidyl ester

50 G (0.20 mol) of 1,3-adamantanediacetic acid, 75 g (0.78 mol) of epichlorohydrin, 5 g of tetraethylammonium bromide, 225 g of toluene, and 48 g of a 50 mass % sodium hydroxide aqueous solution were charged into a 500-mL round bottom flask equipped with a Dean-Stark reflux condenser, a stirrer, a thermometer, and a nitrogen introducing tube. The flask was immersed in an oil bath at 130° C. and was heated to reflux for 3 hours. At that time, a small amount of nitrogen was allowed to flow and the mixture was stirred, and the reaction was performed while removing from the reaction system the water generated along with the progress of the reaction. After that, the reaction solution was cooled to room temperature and washed with water until the aqueous layer became neutral, and then the solvent was distilled off from the organic layer, to thereby obtain an yellow viscous liquid.

Next, the yellow viscous liquid was dissolved in 260 g of toluene, and 15.6 g of a 25 mass % sodium hydroxide aqueous solution were added thereto. The mixture was stirred and heated to reflux in an oil bath at 130° C. for 2 hours. After that, the resultant was cooled to room temperature and washed with water until the alkali aqueous layer became neutral, and then the aqueous layer was further washed with water once more. The solvent was distilled off from the organic layer, to thereby obtain a target product represented by the following formula (yield: 88%, epoxy equivalent of 205).

[Chem 10]

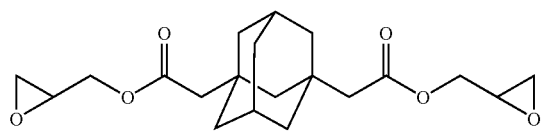

Nuclear magnetic resonance spectra (solvent: $CDCl_3$) JNM-ECA500 manufactured by JEOL LTD.

$^1$H-NMR (500 MHz): 1.52 (m, 12H), 2.07 (s, 2H), 2.15 (s, 4H), 2.64 (dd, 2H), 2.84 (dd, 2H), 3.20 (m, 2H), 3.90 (dd, 2H), 4.39 (dd, 2H)

$^{13}$C-NMR (125 MHz): 28.6, 33.2, 35.5, 41.2, 44.5, 46.9, 47.9, 49.2, 64.4, 170.9

[Production of Cured Product of Resin Composition and Evaluation of Physical Properties Thereof]

In each of the following examples and comparative examples, a cured product of a resin composition was produced, the resin composition containing the adamantane derivative (s) obtained by the above production method, and an epoxy resin curing agent and the like. The evaluation of the physical properties of the cured product was performed as follows.

(1) Glass Transition Temperature (° C.)

A differential scanning calorimeter (manufactured by PerkinElmer Co., Ltd., DSC-7) was used, and a heat flux curve was obtained by retaining 10 mg of a sample under nitrogen atmosphere at 50° C. for 5 minutes and then increasing the temperature at the rate of 10° C./min. A discontinuous point observed in the heat flux curve was taken as a glass transition temperature Tg. was defined as a glass transition temperature Tg.

(2) Light Transmittance (%)

A test piece of 3 mm was used as a sample, and the light transmittance was measured in accordance with JIS K7105. A spectrophotometer UV-3100S (manufactured by Shimadzu Corporation) was used as the measuring instrument, and the measurement was performed at a measurement wavelength of 400 nm.

(3) Light Resistance Test

A sample was measured for its light transmittance at 400 nm by using a sunshine tester (manufactured by Toyo Seiki Seisaku-Sho, Ltd., Suntest CPS+), and after the sample was irradiated with light at 60° C. for 500 hours, the light transmittance was measured by using the sunshine tester in the same manner as above, to thereby compare the change before and after the test. When the decrease rate of the light transmittance was less than 20%, it was evaluated as "o", and when the decrease rate was 20% or more, it was evaluated as "x".

(4) Long-Term Heat Resistance Test

A sample was measured for its light transmittance at 400 nm by using a sunshine tester, and after the sample was left standing in a thermostat at 140° C. for 100 hours, the light transmittance was measured in the same manner as above, to thereby compare the change before and after the test. When the decrease rate of the light transmittance was less than 20%, it was evaluated as "o", and when the decrease rate was 20% or more, it was evaluated as "x".

Example 3

5 G of 1,3,5-adamantanetricarboxylic acid triglycidyl ester obtained in Example 1, 4.87 g of methylhexahydrophthalic anhydride (manufactured by New Japan Chemical Co., Ltd., MH700) as the acid anhydride, 0.1 g of an octylic acid salt of 1,8-diazabicyclo[5.4.0]undecene-7 (manufactured by SAN-APRO Ltd., SA102) as the curing accelerator, and 0.03 g of 2,6-di-t-butyl-4-methylphenol (BHT) as the antioxidant were mixed at room temperature, and the mixture was degassed. After that, the resultant was heated at 110° C. for 2 hours and then at 150° C. for 3 hours, to thereby produce a cured product (sheet having a thickness of 3 mm).

The obtained cured product of the resin composition was measured for its glass transition temperature and light transmittance in accordance with the above measurement methods (1) and (2), respectively, and further, a light resistance test and a long-term heat resistance test were performed in accordance with the above evaluation tests (3) and (4), respectively. Table 1 shows the evaluation results.

Example 4

A cured product was produced in the same manner as in Example 3, except that: the amount of 1,3,5-adamantanetricarboxylic acid triglycidyl ester was changed to 2.5 g; 2.5 g of 1,3-adamantanediacetic acid diglycidyl ester obtained in Example 2 was further added to the mixture; and the amount of methylhexahydrophthalic anhydride was changed to 4.42 g. The same evaluation test was performed on the cured product. Table 1 shows the evaluation results.

Comparative Example 1

A cured product was produced in the same manner as in Example 3, except that: 1,3,5-adamantanetricarboxylic acid triglycidyl ester was changed to 5 g of a bisphenol A epoxy resin (manufactured by Japan Epoxy Resins Co., Ltd., EPIKOTE 828); and the amount of methylhexahydrophthalic anhydride was changed to 4.40 g. The same evaluation test was performed on the cured product. Table 1 shows the evaluation results.

Comparative Example 2

A cured product was produced in the same manner as in Example 3, except that: 1,3,5-adamantanetricarboxylic acid triglycidyl ester was changed to 5 g of a hydrogenated bisphenol A epoxy resin (manufactured by Japan Epoxy Resins Co., Ltd., EPIKOTE YX8000); and the amount of methylhexahydrophthalic anhydride was changed to 4.01 g. The same evaluation test was performed on the cured product. Table 1 shows the evaluation results.

TABLE 1

|  | Example 3 | Example 4 | Comparative Example 1 | Comparative Example 2 |
| --- | --- | --- | --- | --- |
| Glass transition temperature (° C.) | 161 | 152 | 140 | 105 |
| Light transmittance (%) | 90 | 91 | 80 | 92 |
| Light resistance test | ○ | ○ | x | ○ |
| Long-term heat resistance test | ○ | ○ | ○ | x |

INDUSTRIAL APPLICABILITY

The adamantane derivative having a cyclic ether group of the present invention and the resin composition containing the derivative and an epoxy resin curing agent of the present invention are excellent in optical characteristics such as transparency and light resistance, durabilities such as heat resistance, and electrical characteristics such as dielectric constant, and are suitable for the optical electronic members such as a lens for optical communication and an optical film, by being served as the sealing agent and the adhesive agent for an optical semiconductor (such as LED), an organic EL device, an optical circuit (optical waveguide), and an electronic circuit. In addition, the adamantane derivative and the resin composition have etching resistance, and hence are useful as semiconductor forming materials such as a sealing agent for a semiconductor and an anti-reflection film for a semiconductor.

The invention claimed is:

1. An adamantane derivative represented by the following general formula (I):

[Chem 1]

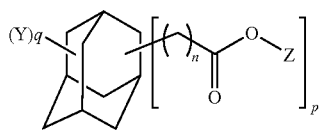
(I)

where: Y represents a group selected from a hydrocarbon group having 1 to 10 carbon atoms, a hydroxyl group, a carboxyl group, and an =O group formed by two Y's being combined together, and a plurality of Y's may be identical to or different from each other;

Z is represented by the following general formula (II) or (III):

[Chem 2]

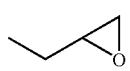
(II)

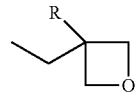
(III)

where R represents a hydrogen atom or an alkyl group having 1 to 4 carbon atoms;

n represents an integer of 0 or more; and p represents an integer of 2 to 4 and q represents an integer of 0 to 14, while satisfying $2 \leq p+q \leq 16$, provided that n=0 and p=2 are not satisfied at the same time.

2. A method of producing the adamantane derivative according to claim 1, comprising reacting an adamantane derivative having a carboxyl group represented by the following general formula (IV) with a compound having a cyclic ether group represented by the following general formula (V) or (VI):

[Chem 3]

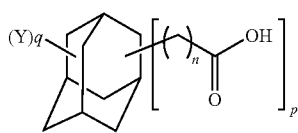
(IV)

where Y, n, p, q, and p+q each represent the same as above; and

[Chem 4]

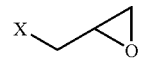
(V)

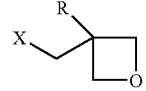
(VI)

where X represents a halogen atom, a mesyl group, or a tosyl group, and R represents the same as above.

3. A resin composition, comprising:
the adamantane derivative according to claim 1; and
an epoxy resin curing agent.

4. A sealing agent for an optical semiconductor, which is formed by using the resin composition according to claim 3.

5. An optical electronic member, which is formed by using the resin composition according to claim 3.

6. A sealing agent for an electronic circuit, which is formed by using the resin composition according to claim 3.

* * * * *